US006448076B2

(12) United States Patent
Dennis et al.

(10) Patent No.: US 6,448,076 B2
(45) Date of Patent: Sep. 10, 2002

(54) METHOD FOR CHEMICALLY ACELLULARIZING A BIOLOGICAL TISSUE SAMPLE

(75) Inventors: Robert G. Dennis, Ann Arbor; William M. Kuzon, Jr., Dexter; Paul S. Cederna, Ann Arbor, all of MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 0 days.

(21) Appl. No.: 09/896,651

(22) Filed: Jun. 29, 2001

Related U.S. Application Data

(60) Continuation-in-part of application No. 09/709,890, filed on Nov. 9, 2000, which is a division of application No. 09/153,721, filed on Sep. 15, 1998, now Pat. No. 6,207,451.

(51) Int. Cl.$^7$ ................................................ C12N 5/00
(52) U.S. Cl. ........................ 435/325; 435/368; 435/395
(58) Field of Search ................................ 435/325, 368, 435/395

(56) References Cited

U.S. PATENT DOCUMENTS

| | | | |
|---|---|---|---|
| 3,960,151 A | | 6/1976 | Kuhn |
| 4,605,623 A | | 8/1986 | Malette et al. |
| 4,642,292 A | * | 2/1987 | Reid et al. |
| 4,759,764 A | | 7/1988 | Fawcett et al. |
| 4,776,853 A | | 10/1988 | Klement et al. |
| 4,801,299 A | * | 1/1989 | Brendel et al. |
| 4,870,966 A | | 10/1989 | Dellon et al. |
| 4,940,853 A | | 7/1990 | Vandenburgh |
| 4,963,146 A | | 10/1990 | Li |
| 5,019,087 A | | 5/1991 | Nichols |
| 5,026,381 A | | 6/1991 | Li |
| 5,147,399 A | | 9/1992 | Dellon et al. |
| 5,153,136 A | | 10/1992 | Vandenburgh |
| 5,336,616 A | | 8/1994 | Livesey et al. |
| 5,443,950 A | | 8/1995 | Naughton et al. |
| 5,618,718 A | | 4/1997 | Auger et al. |
| 5,756,350 A | | 5/1998 | Lee et al. |
| 5,840,689 A | | 11/1998 | Daniloff |
| 6,033,660 A | | 3/2000 | Mather et al. |
| 6,095,148 A | | 8/2000 | Shastri et al. |
| 6,214,021 B1 | | 4/2001 | Hadlock et al. |
| 6,241,981 B1 | | 6/2001 | Cobb et al. |

OTHER PUBLICATIONS

Adarsh K. Gulati, Evaluation of Acellular and Cellular Nerve Grafts in Repair of Rat Peripheral Nerve, J. Neurosurg., vol. 68, Jan., 1988, pp. 117–123.*
Adarsh K. Gulati et al., Immunogenicity and Regenerative Potential of Acellular Nerve Allografts to Repair Peripheral Nerve in Rats and Rabbits, Acta Neurochir., vol. 126, 1994, pp. 158–164.*
Vaishali B. Doolabh et al., The Role of Conduits in Nerve Repair: A Review, Reviews in the Neurosciences, vol. 7, No. 1, 1996, pp. 47–84.*

Peter J. Evans et al., The Peripheral Nerve Allograft: A Comprehensive Review of Regeneration and Neuroimmunology, Progress in Neurobiology, vol. 43, 1994, pp. 187–233.*
Robert A. Weber et al., A Randomized Prospective Study of Polyglycolic Acid Conduits for Digital Nerve Reconstruction in Humans, Plastic and Reconstructive Surgery, vol. 106, Oct., 2000, pp. 1036–1045.*
Peter J. Evans et al., Cold Preserved Nerve Allografts: Changes in Basement Membrane, Viability, Immunogenicity, and Regeneration, Muscle & Nerve, vol. 21, Nov., 1998, pp. 1507–1522.*
Karen L. Gibson et al., Comparison of Nerve Regeneration Through Different Types of Neural Prostheses, Microsurgery, vol. 12, 1991, pp. 80–85.*
Susan Hall, Axonal Regeneration Through Acellular Muscle Grats, J. Anat., vol. 190, 1997, pp. 57–71.*
Y. Takami et al., Dispase/Detergent Treated Dermal Matrix as a Dermal Substitute, Burns, vol. 22, No. 3, 1996, pp. 182–190.*
Adarsh K. Gulati et al., The Influence of Cultured Schwann Cells on Regneration through Acellular Bsal Lamina Grafts, Brain Research, vol. 705, 1995, pp. 118–124.*
Mary Bartlett Bunge et al., Schwann Cell Function Depends upon Axonal Signals and Basal Lamina Components, Annals of the New York Academy of Sciences, vol. 580, 1990, pp. 281–287.*
David T. W. Chiu et al., Autogenous Vein Graft as a Conduit for Nerve Regeneration, Surgery, vol. 91, 1982, pp. 226–233.
Susan E. MacKinnon et al., A Study of Nerve Regeneration Across Synthetic (Maxon) and Biologic (Collagen) Nerve Conduits for Nerve Gaps Up to 5 cm in the Primate, Journal of Reconstructive Microsurgery, vol. 6, No. 2, Apr., 1990, pp. 117–121.
Mariann Sondell et al., Regeneration of the Rat Sciatic Nerve into Allografts Made Acellular through Chemical Extraction, Brain Research, vol. 795, 1998, pp. 44–54.
Steven C. Haase et al., Peripheral Nerve Reconstruction Using Acellular Nerve Grafts, Surgical Forum, vol. 51, 2000, pp. 607–609.
S. Haase et al., Repair of Nerve Gaps with Acellular Nerve Grafts, Bi–Annual Scientific Meeting, Reed O. Dingman Society, Sep. 7–9, 2000, Ann Arbor, MI.

(List continued on next page.)

Primary Examiner—Leon B. Lankford, Jr.
(74) Attorney, Agent, or Firm—Brooks & Kushman P.C.

(57) ABSTRACT

A method for chemically acellularizing a biological tissue sample, such as a peripheral nerve, is provided. The method includes disrupting the cell membranes of the biological tissue sample, and then denaturing intracellular proteins within the cells of the tissue sample and removing the denatured proteins from the cells while preserving the extracellular matrix to produce an acellularized tissue construct.

21 Claims, 3 Drawing Sheets

OTHER PUBLICATIONS

J. Rovak et al., Acellularized Peripheral Nerve Allograft Repopulated with Isogenic Schwann Cells: A Non–Immunogenic Construct that Supports Axonal Growth Across Short Nerve Gaps, Leiden International Medical Students Congress, Mar. 16–17, 2001, Leiden, Netherlands.

J. Rovak et al., The Immunologic Response to Chemically Acellularized Peripheral Nerve, 2001 Annual Moses Gunn Research Conference, May 1, 2001, The University of Michigan, Ann Arbor, MI.

J. Rovak et al., Chemical Acellurlarization of Peripheral Nerve: A Method for Eliminating Graft Alloantigens, $46^{th}$ Annual Meeting, Plastic Surgery Research Council, Jun. 9–12, 2001, Milwaukee, Wisconsin.

Adarsh K. Gulati, Immune Response and Neurotrophic Factor Interactions in Peripheral Nerve Transplants, Acta Haematol., vol. 99, 1998, pp. 171–174.

Charles E. Dumont et al., A Composite Nerve Graft System: Extracted Rat Peripheral Nerve Injected with Cultured Schwann Cells, Muscle & Nerve, vol. 19, Jan. 1996, pp. 97–99.

Charles E. Dumont et al., Enhancement of Axon Growth by Detergent–Extracted Nerve Grafts, Transplantation, vol. 63, No. 9, May 15, 1997, pp. 1210–1215.

P.C. Johnson et al., Preparation of Cell–Free Extracellular Matrix from Human Peripheral Nerve, Muscle & Nerve, vol. 5, Apr., 1982, pp. 335–344.

Vandenburgh, Hatfaludy, Karlisch and Shansky; "Skeletal Muscle Growth Is Stimulated By Intermittent Stretch Relazation In Tissue Culture"; American Psych. Society; 1989; pp. C674–C682.

Vandenburgh; "A Computerized Mechanical Cell Stimulator For Tissue Culture Effects On Skeletal Muscle Organogenesis"; In Vitro Cellular & Developmental Biology; vol. 24; No. 7; Jul. 1988; pp. 609–619.

Vandenburgh and Karlisch; "Longitudinal Growth of Skeletal Myotubes In Vitro In A New Horizontal Mechanical Cell Stimulator"; In Vitro Cell Dev. Bio.; vol. 25; No. 7; Jul. 1989; pp. 607–616.

Vandenburgh, Swasdison and Karlisch; "Computer–Aided Mechanogenesis of Skeletal Muscle Organs From Single Cells In Vitro"; The FASEB Journal; vol. 5; Oct. 1991; pp. 2860–2867.

Vandenburgh, Tatto, Shansky, Lemaire, Chang, Payum, Lee, Goodyear and Raven; "Tissue–Engineered Skeletal Muschle Organoids For Reversible Gene Therapy"; Human Gene Therapy; Nov. 1996; pp. 2195–2200.

* cited by examiner

METHOD FOR CHEMICALLY ACELLULARIZING A BIOLOGICAL TISSUE SAMPLE

CROSS-REFERENCE TO RELATED APPLICATIONS

This application is a continuation-in-part of U.S. application Ser. No. 09/709,890 filed Nov. 9, 2000, which is a divisional of U.S. application Ser. No. 09/153,721 filed Sep. 15, 1998, now U.S. Pat. No. 6,207,451.

STATEMENT REGARDING FEDERALLY SPONSORED RESEARCH OR DEVELOPMENT

The invention was made with Government support under Grant No. NS34380 from the National Institute of Neurologic Disease and Stroke and Grant No. T32 A7G01 14 from the the National Institute of Health. The Government has certain tights in this invention.

BACKGROUND OF THE INVENTION

1. Field of the Invention

This invention r elates to the field of tissue engineering, and more particularly to a method for chemically acellularizing a biological tissue sample, such as a peripheral nerve.

2. Background Art

Peripheral nerve injuries are exceedingly common, occurring clinically after injury or surgical resection. The resulting nerve gaps can produce significant disability and thus require surgical repair. Primary end-to-end nerve coaptation is the procedure of choice for peripheral nerve reconstruction, but in many circumstances the gap between the proximal and distal stump is too large to allow for a tension-free repair. Under these circumstances, surgeons must employ alternate repair techniques, such as nerve grafting.

Peripheral nerve autografts are the g old standard for nerve grafting procedures and provide the optimal degree of reinnervation when primary end-to-end neurorrhaphy is not an option. However, the functional deficits at the donor site following nerve graft harvest as well as the limited amounts of donor nerve tissue available restrict the use of autografts in many clinical situations.

To avoid the problems inherent in autografting, surgeons have investigated different methods of repair such as termino-lateral neurorrhaphy (TLN) and autogenous vein and plastic chamber conduits. TLN entails suturing the distal stump of a severed nerve to the side of an intact adjacent nerve which is not always available . Autogenous vein grafts and plastic chambers are a plentiful supply of nerve regeneration conduits, yet neither provides the trophic support (nerve growth factor, etc.) necessary for axonal regeneration across nerve gaps greater than 2 cm, leading to poor functional outcomes.

Peripheral nerve allografts provide another alternative for nerve repair. Although allografts overcome the problems associated with the previously mentioned repair methods, nerve allograft rejection becomes a major obstacle. Until long term tolerance to nerve allografts can be induced, this technique requires long term systemic immunosuppression and as a result has limited clinical applications.

Acellular nerve grafts, produced by a variety of techniques, have emerged as a possible alternative to overcome the immnunogenicity of allografts. Previous attempts to create acellular nerve tissue have involved several methods, namely irradiation, fixation, heat treatment, or freezing, prior to grafting in an effort to kill or remove the cellular elements of the nerve allograft and reduce immunogenicity. Peripheral nerve grafts that have been acellularized by such methods have been shown to support axonal regeneration across short distances and to elicit a reduced immune response compared with standard peripheral nerve allografts. However, these acellularization methods cause disruption of the cellular elements of the nerve and may concurrently disrupt the endoneurial tubes, thus reducing the potential for axonal elongation through the nerve graft. In addition, cellular debris remaining after the mechanical disruption process may also elicit an immune response which can adversely affect Schwann cell migration and axonal elongation.

SUMMARY OF THE INVENTION

Therefore, it is an object according to the present invention to provide a method for chemically acellularizing a biological tissue sample which does not rely on mechanical cell disruption.

It is a further object according to the present invention to provide a method of acellularization which removes the cellular elements from peripheral nerve tissue while leaving the endoneurial architecture intact.

It is another object according to the present invention to provide an acellularization method which produces an acellularized peripheral nerve construct that will support axonal regeneration across nerve gaps.

It is still another object according to the present invention to provide an acellularization method which produces an acellularized peripheral nerve construct that is nonimmunogenic.

Accordingly, a method is provided for chemically acellularizing a biological tissue sample, such as a peripheral nerve. The method includes disrupting the cell membranes of the biological tissue sample, and then denaturing intracellular proteins within the cells of the tissue sample and removing the denatured proteins from the cells while preserving the extracellular matrix to produce an acellularized tissue construct without using mechanical agents.

In a preferred embodiment, the tissue sample is harvested from a suitable donor, and then submersed in a balanced salt solution, such as Dulbecco's phosphate buffered saline. The disrupting of cell membranes then includes submersing the biological tissue sample in a solution including glycerol, whereas denaturing and removing intracellular proteins includes submersing the biological tissue in at least one detergent solution. The one or more detergent solutions can comprise ionic detergent solutions and nonionic detergent solutions. Most preferably, the tissue sample is submersed in a succession of ionic and nonionic solutions, where the ionic detergent solutions can include sodium deoxycholate or sodium dodecyl sulfate, and the nonionic detergent solutions can include TRITON® X-100. In addition, the biological tissue sample is preferably rinsed with distilled water between each solution change. The resulting acellularized tissue construct can then be stored in a physiologic saline solution, and later implanted in a suitable recipient.

The above objects and other objects, features, and advantages of the present invention are readily apparent from the following detailed description of the best mode for carrying out the invention when taken in connection with the accompanying drawings.

DETAILED DESCRIPTION OF THE PREFERRED EMBODIMENT(S)

Figure 1A:
FIGS. 1a and 1b are electron micrographs of a peripheral nerve prior to and following acellularization, respectively, according to the method of the present invention.

A method of acellularization and the acellularized peripheral nerve construct formed thereby are described herein. The acellularization method of the present invention is a chemical, rather than a mechanical, process that generally involves submersion of peripheral nerve tissue in a glycerol solution followed by a series of detergents and other reagents to disrupt and digest the cellular elements of the nerve. As shown and described herein, the removal of cellular elements by this method does not disrupt the endoneurial matrix which is necessary to support and guide axonal regeneration. Therefore, the immunogenicity of the peripheral nerve construct of the present invention is eliminated by the removal of cellular elements, but the ability to support nerve regeneration is maintained.

The following description and experimental results illustrate the efficacy of the chemical acellularization method of the present invention and the resulting peripheral nerve construct using nerve tissue harvested from and subsequently implanted in rats. Of course, it is fully contemplated that peripheral nerve tissue from any mammal, including human beings, could be similarly acellularized and grafted using the method described herein.

To produce the acellular nerve constructs according to the present invention, 100 mm culture dishes are first prepared by mixing and pouring approximately 20 ml of SYLGARD® (Dow Corning, Midland, Mich.) into the dishes, wherein the SYLGARD® is allowed to air dry and harden for at least one week prior to use of the dishes. Under general anesthesia and aseptic conditions, rat peripheral nerve segments are then surgically removed, pinned at slack length (straight, but not taut) within the culture dishes using minutien pins, and immediately submersed in Dulbecco's Phosphate Buffered Saline (PBS) or another suitable balanced salt solution.

The following acellularization method is carried out at room temperature (~21° C.) within covered culture dishes. Advantageously, the acellularization method described herein is simple, inexpensive, uses commonly available chemicals of low toxicity, and does not require mechanical agents of any kind. Accordingly, in order to remove the cellular material, the following solutions are prepared and stored at room temperature, wherein $NaN_3$ is used in each solution as a preservative:

Solution 1: 7.3 g EDTA
   0.5 g $NaN_3$
   800 ml Glycerol
   200 ml 0.9% NaCl
Solution 2: 25 g Sodium deoxycholate (ionic detergent)
   0.26 g $NaN_3$
   600 ml distilled $H_2O$
Solution 3: 10 g sodium dodecyl sulfate (SDS) (ionic detergent)
   0.52 g $NaN_3$
   1000 ml distilled $H_2O$
Solution 4: 15 ml TRITON® X-100 (nonionic detergent)
   0.25 g $NaN_3$
   485 ml distilled $H_2O$
Solution 5: 0.5 g $NaN_3$
   1000 ml 0.9% NaCl First, the peripheral nerve segments are submersed with Solution 1 for approximately 72 hours in order to disrupt the cell membrane. Second, the nerve segments are submersed with Solution 2 for approximately 72 hours to begin intracellular protein dissociation. Between each solution change, the nerve segments were rinsed at least once with distilled water. Next, the nerve segments are again submersed with Solution 1, this time for approximately 48 hours to complete the removal of lipid-soluble cell structures. The nerve segments are then submersed with Solution 3 for approximately 48 hours for additional protein denaturing. Subsequently, the nerve segments are submersed with Solution 4 for approximately 48 hours in order to remove denatured proteins from the extracellular matrix, leaving the extracellular matrix intact. The nerve segments are next submersed with Solution 3 for approximately 48 hours to accomplish final protein denaturing and removal. Lastly, the nerve segments are submersed with Solution 5 where they can be stored for at least 4 weeks until use, wherein Solution 5 may be added as necessary to prevent evaporation.

Due to the technical design of the acellularization method according to the present invention, there should be no limitations on the length or diameter of nerve grafts that can be created. Larger diameter nerve grafts can be acellularized by simply employing correspondingly longer immersion times for each solution.

Of course, it is understood that all reagent measurements and submersion times described above are approximate, and can be varied slightly without affecting the resulting acellularization. The chemical acellularization method according to the present invention was utilized in the context of acellularizing muscle tissue in commonly assigned U.S. Pat. No. 6,207,451 which is incorporated by reference herein.

To functionally and histologically evaluate the acellularized nerve construct produced by the chemical acellularization method of the present invention, several experiments were performed. By examining the corresponding muscle force generation following nerve graft repair as well as muscle and nerve histology, microscopic structure can be correlated with functional results.

Experiments were performed using adult male, specific-pathogen-free Fischer-344 rats (Charles River Laboratory, Kingston, N.Y.). For each animal, the left peroneal nerve was exposed and a 2 cm segment was excised to create a nerve gap and serve as a model for traumatic nerve injury. An identical length of acellularized nerve was used to repair the nerve gap. The proximal and distal ends of the peroneal nerve stumps were coapted to the proximal and distal ends of the graft in the standard end-to-end fashion using 10-0 nylon epineurial sutures. A 15 week recovery period was allowed following the initial surgery prior to measuring muscle contractile properties and analyzing muscle and nerve histology.

Walking tracks were used to evaluate integrated motor function preoperatively and at 15 weeks postoperatively using standard protocols. Individual walking track records were digitally scanned into high-resolution computer graphic files, and measurements were performed at 2× resolution using SigmaScan Pro (Version 4.10.003, 1997, SPSS Inc.) image analysis software. For each record, 3 or 4 footprints during a period of brisk walking were used for analysis. For each footprint, the intermediate toe spread (ITS) was measured from the tip of the second toe to the tip of the fourth toe bilaterally on both the nerve grafted leg (left) and unoperated leg (right). The functional ITS index was then calculated for each walking track record using the formula ITS index=(Left ITS−Right ITS)/Right ITS. The results showed that the average ITS index value at 15 weeks following acellular nerve grafting was decreased only approximately 20% compared with the preoperative baseline value, thereby confirming at least partial recovery of integrated function using the acellular nerve grafts of the present invention.

Extensor digitorum longus (EDL) muscle contractile function was also analyzed in situ 15 weeks following the initial nerve graft surgery to determine the extent of muscle reinnervation following peripheral nerve injury and repair. Each rat was anesthetized, the left EDL was isolated, and the distal tendons of the EDL were divided and folded to create a tendon loop which was secured at the musculotendinous junction with 3-0 silk suture. The tibial and sural nerves, as well as the distal tendon of the tibialis anterior muscle were then divided to avoid motion artifact. The rat was placed on a platform maintained at~37° C. by a temperature-controlled water circulator, and the EDL tendon loop was secured to the force transducer. Throughout the evaluation, muscle temperature was monitored and maintained between approximately 35° and 37° C.

The EDL muscles were activated indirectly by delivering supramaximal electrical stimuli (square pulses, 0.2 msec pulse duration, 6–10 V) to the peroneal nerve proximal to the graft site. Stimuli were generated by a Grass S88 Stimulator (Grass Instrument Co., Quincy, Mass.) and delivered with a shielded bipolar silver wire electrode (Harvard Apparatus, South Natick, Mass.). Output from the force transducer was sampled by means of an analog-to-digital converter (Data Translation, Marlboro, Mass.) interfaced with a microcomputer. Custom software (Asyst Software Technologies, Inc., Rochester, N.Y.) was used to control data collection and to perform signal analysis. At optimal muscle length ($L_O$), maximum tetanic isometric force ($F_O$) was evaluated by stimulating the EDL muscle for 250 msec at increasing frequencies (from 30 to 350 Hz) and determining the highest force generated. Following the force measurements, the muscles were excised, the tendons trimmed, and the muscles were weighed. The results showed that at 15 weeks postoperatively the EDL muscle mass was 72.8±22.6 mg and $F_O$ was 726.3±608.1 mN. Although decreased compared with values for sham-operated control animals, the recovery of force generating capabilities of EDL muscles reinnervated using acellularized nerve grafts according to the present invention assures that the regenerating axons have made functional connections with the target muscle.

Subsequent to the above procedures, the nerve grafts were fixed in a formaldehyde/glutaraldehyde solution, then rinsed within 24 hours and transferred to storage buffer. The fixed nerves were then hydrated using graded ethanol baths prior to embedding in epoxy. Thin (10 μm) sections taken from the distal end of the nerve grafts were then mounted and stained with toluidine blue for quantitative analysis. Nerve sections also underwent electron microscopic analysis to assess nerve graft axon population as well as degree of myelination.

Figure 1B:
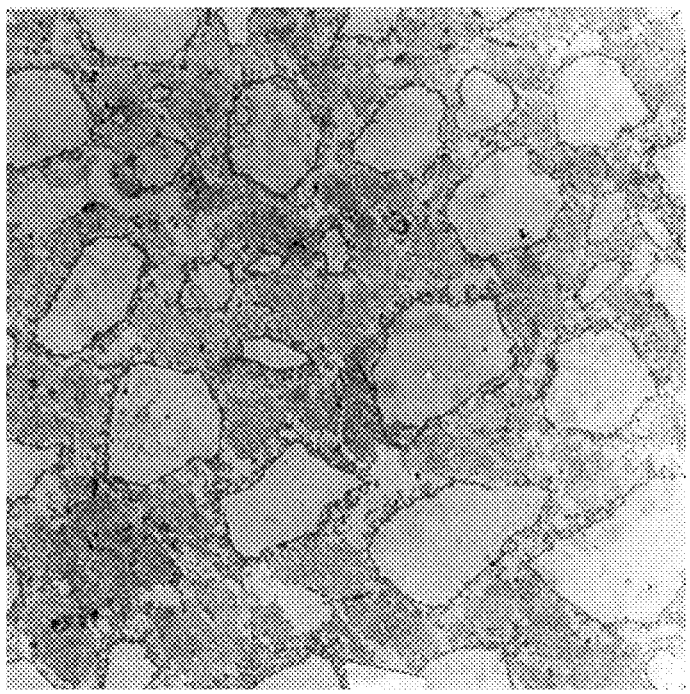

Referring now to FIGS. 1a and 1b, electron micrographs of representative peripheral nerves prior to and following, respectively, the chemical acellularization method of the present invention are shown. As one skilled in the art will readily observe, FIG. 1a depicts myelinated axons traversing the length of the nerve, while FIG. 1b shows a lack of cellular elements and preserved endoneurial sheaths and basal lamina within the nerve. This analysis indicates that the majority of the intracellular and cell membrane components are removed by the chemical acellularization method utilized herein. The remaining material is principally extracellular matrix (ECM) which provides the structural support for nerve regeneration. Therefore, the acellularization method of the present invention appears to remove the Schwann cells in order to reduce the immunogenicity of the construct, but preserves the basal lamina in order to maintain the appropriate molecular signals and adhesion molecules to enhance axonal regeneration. Presumably, the preserved basal lamina provides the appropriate adhesion molecules and molecular signals to promote Schwann cell migration, differentiation, and ultimately axonal elongation.

Figure 2:
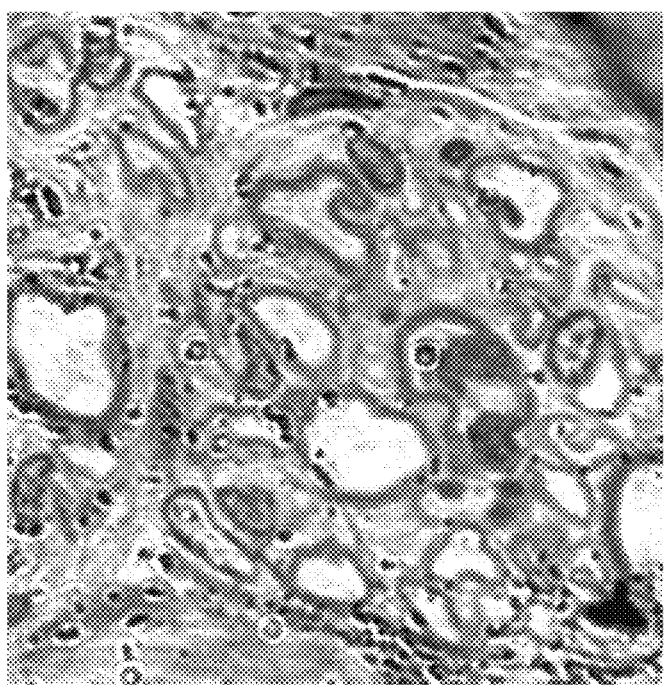
FIG. 2 is a toluidine blue stain of a distal end of an acellular nerve graft according to the present invention.

With reference to FIG. 2, a toluidine blue stained section of the distal end of a representative acellular nerve graft is shown 15 weeks after the construct was used to reconstruct a gap in a rat peroneal nerve, wherein the section was taken approximately 2 cm distal to the nerve coaptation site. Multiple large and small myelinated axons can be readily observed by one skilled in the art, thereby demonstrating the ability of the acellularized nerve grafts to support axonal regeneration and to allow end-organ reinnervation.

Figure 3:
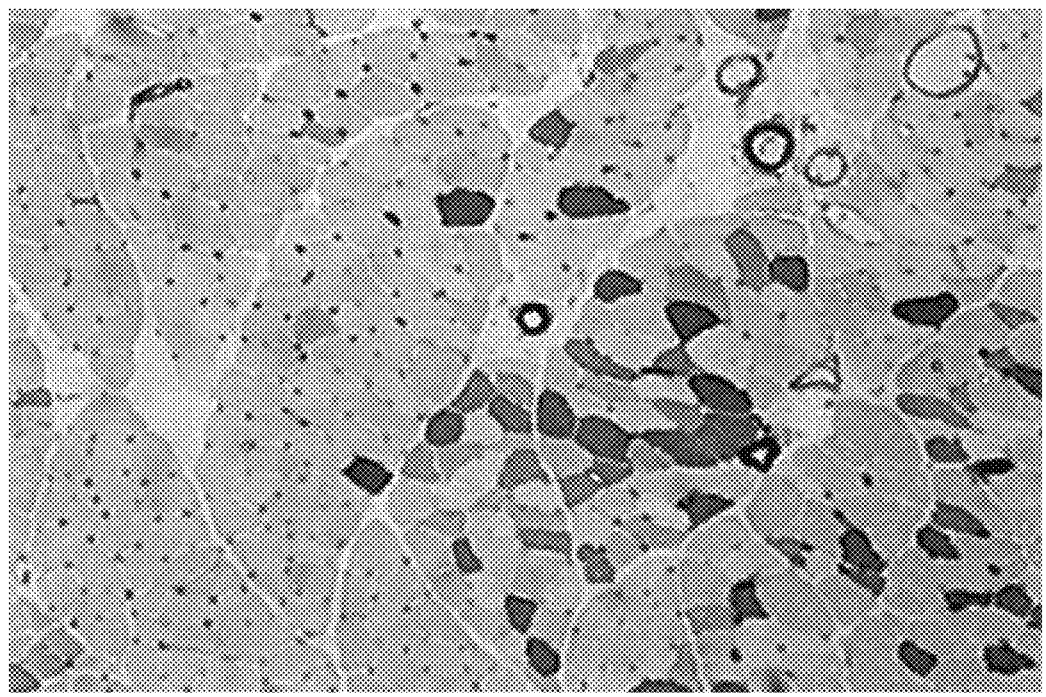
FIG. 3 is a myosin ATPase stain (pH=4.3) of a rat extensor digitorum longus muscle following repair of a peroneal nerve gap with an acellularized nerve graft according to the present invention.

Following the force measurements, the EDL muscles were covered with cryopreservative, frozen with isopentane cooled by liquid nitrogen (−160° C.), and stored at −60° C. for subsequent processing. Whole EDL muscle cross-sections (12 μm thick) were cut using a cryotome (−20° C.), then stained with hematoxylin & eosin and myosin ATPase using standard techniques for subsequent light microscopic fiber type analysis. With reference to FIG. 3, a myosin ATPase stained section (pH=4.3) of a representative EDL muscle is shown, wherein areas of large polygonal muscle fibers loosely grouped according to muscle fiber type are readily evident to those skilled in the art. Such a spatial distribution of fiber types is characteristic of reinnervated muscle.

Therefore, the functional and histological data described above clearly demonstrate that the chemically acellularized nerve grafts of the present invention support axonal regeneration across at least a 2 cm nerve gap and that functional muscle reinnervation can be achieved.

Figure 4:
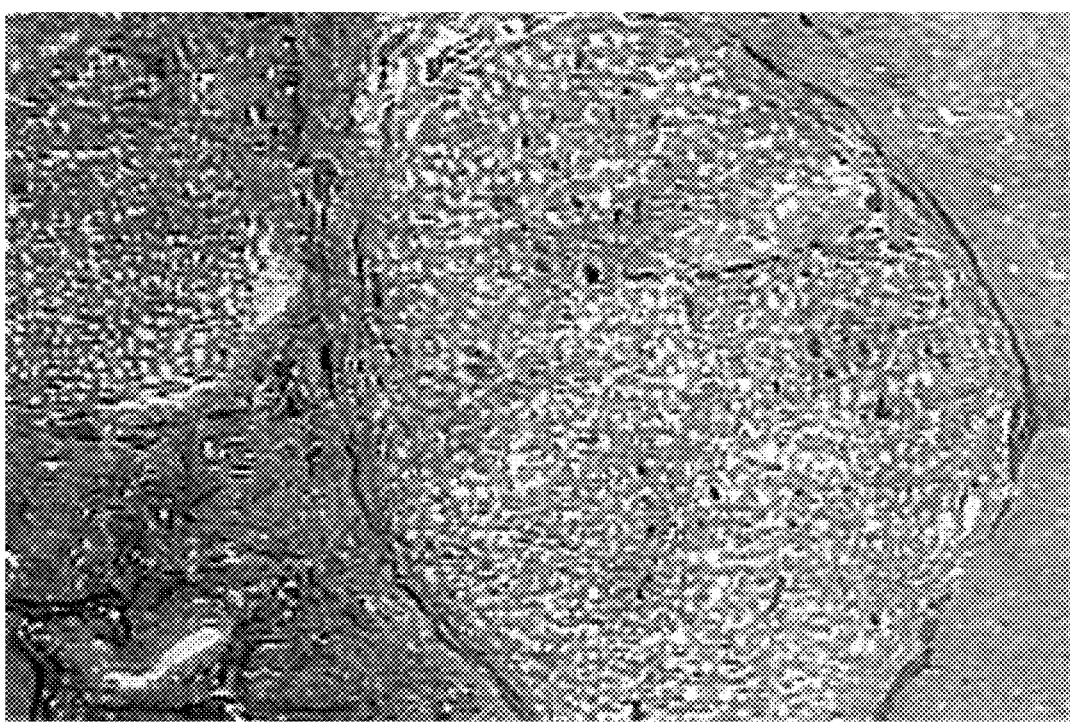
FIG. 4 is a light micrograph of an acellularized peripheral nerve construct according to the present invention following transplantation across a major histocompatibility barrier.

To evaluate immunogenicity, acellularized nerve constructs according to the present invention were transplanted into subcutaneous pockets across a major histocompatibility barrier, from ACI rat donors to Lewis rat recipients. Referring now to FIG. 4, a light micrograph of a section of a representative acellular nerve construct displays no evidence of an inflammatory response or any other acute or chronic rejection response. This preliminary experiment demonstrates that the acellularization method of the present invention produces a nerve construct that is nonimmunogenic when transplanted across major histocompatibility antigen barriers, thus immunosuppressive drugs should not be required. Such grafts also demonstrate axonal regeneration and successful reinnervation of the motor end organ via the nerve graft as described for the previous experiments.

Therefore, the chemically acellularized nerve constructs described herein support axonal regeneration and functional reinnervation for the reconstruction of peripheral nerve gaps. The chemical acellularization method according to the present invention provides a scaffold for axonal regeneration that is more suitable than that left by mechanical acellularization processes while removing all of the immunologically reactive cellular components. More particularly, the chemical acellularization method appears to preserve the delicate ultrastructure of peripheral nerves while removing the most antigenic components, namely the Schwann cells and myelin. Furthermore, the acellularization method of the present invention produces a nerve construct that induces no histologically evident acute or chronic rejection response when transplanted across major histocompatibility antigen barriers.

Schwann cells produce many neurotrophic factors that aid in axonal regeneration, including NGF, IGF, and CNTF. By reintroducing Schwann cells into the acellularized peripheral nerve grafts of the present invention, axonal regeneration and muscle reinnervation may be further enhanced. Additional strategies to enhance the efficacy of the acellular grafts of the present invention might include reintroducing critical growth factors into the construct through tissue culture techniques or gene derived matrices.

The chemical acellularization method discussed herein could easily be adapted for use in clinical situations where nerve gaps are identified. Applications for the nerve construct and acellularization method of the present invention include peripheral nerve reconstruction after traumatic injury, reconstruction of nerve defects resulting from the resection of malignant tumors, functional reconstruction for patients with congenital syndromes where peripheral nerves are absent (e.g., Mobius Syndrome), and for the amelioration of facial paralysis and other movement disorders in some circumstances of CNS injury including strokes and spinal cord injuries. Under these circumstances, sufficient amounts of autologous nerve graft may not be present, and a nonimmunogenic, acellularized human, cadaveric allograft could be utilized for this peripheral nerve reconstruction. In addition, the acellularized nerve grafts could be created from donor nerves that match the recipient nerve to be reconstructed, thus the basic architecture of the nerve graft would be specific to the site of transplantation.

While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention.

What is claimed is:

1. A method for chemically acellularizing a peripheral nerve sample to produce an acellularized peripheral nerve construct, the method comprising:
    disrupting the cell membranes of the peripheral nerve sample by submersing the sample in a solution including glycerol; and
    denaturing intracellular proteins within the cells of the sample and removing the denatured proteins from the cells while preserving the extracellular matrix to produce the acellularized peripheral nerve construct.

2. The method according to claim 1, wherein denaturing and removing intracellular proteins includes submersing the biological tissue in at least one detergent solution.

3. The method according to claim 2, wherein the at least one detergent solution includes sodium deoxycholate.

4. The method according to claim 3, wherein the at least one detergent includes sodium dodecyl sulfate.

5. The method according to claim 2, wherein the at least one detergent solution includes TRITON® X-100.

6. The method according to claim 1, further including harvesting the tissue sample from a suitable donor.

7. The method according to claim 1, further including submersing the tissue sample in a balanced salt solution prior to disrupting the cell membranes.

8. The method according to claim 7, wherein the balanced salt solution includes Dulbecco's phosphate buffered saline.

9. The method according to claim 1, further including storing the acellularized peripheral nerve construct in a physiologic saline solution.

10. The method according to claim 1, further including implanting the acellularized peripheral nerve construct in a suitable recipient.

11. A method for producing a chemically acellularized peripheral nerve construct, the method comprising:
    harvesting a peripheral nerve sample from a donor;
    submersing the peripheral nerve sample in a glycerol solution for disrupting the cell membranes of the peripheral nerve; and
    submersing the peripheral nerve sample in at least one detergent solution for denaturing the intracellular proteins of the cells of the peripheral nerve and removing the denatured proteins while leaving the extracellular matrix intact to produce the acellularized peripheral nerve construct without using mechanical agents.

12. The method according to claim 11, wherein the at least one detergent solution includes a nonionic detergent.

13. The method according to claim 12, wherein the nonionic detergent includes TRITON® X-100.

14. The method according to claim 11, wherein the at least one detergent solution includes an ionic detergent.

15. The method according to claim 14, wherein the ionic detergent includes sodium deoxycholate.

16. The method according to claim 14, wherein the ionic detergent includes sodium dodecyl sulfate.

17. The method according to claim 11, wherein submersing the peripheral nerve sample in at least one detergent solution includes submersing the sample in a succession of solutions including at least one ionic detergent solution and at least one nonionic detergent solution.

18. The method according to claim 17, wherein the succession of solutions includes a sodium deoxycholate solution, a sodium dodecyl sulfate solution, and a TRITON® X-100 solution.

19. The method according to claim 11, further including rinsing the peripheral nerve sample with distilled water between each solution change.

20. A method for producing a chemically acellularized peripheral nerve construct, comprising:
    harvesting a peripheral nerve segment from a donor;
    disrupting the cell membranes and removing lipid-soluble cell structures of the peripheral nerve segment using a glycerol solution;
    denaturing intracellular proteins within the cells of the peripheral nerve segment using at least one ionic detergent; and
    removing the denatured proteins from the cells while leaving the extracellular matrix intact using ionic and nonionic detergents to produce the acellularized peripheral nerve construct without using mechanical agents.

21. The method according to claim 20, further comprising grafting the acellularized peripheral nerve construct within a recipient nerve.

* * * * *